(12) United States Patent
Reddy et al.

(10) Patent No.: US 10,000,579 B2
(45) Date of Patent: Jun. 19, 2018

(54) INTEGRATED PROCESS TO RECOVER A SPECTRUM OF BIOPRODUCTS FROM FRESH SEAWEEDS

(71) Applicant: COUNCIL OF SCIENTIFIC & INDUSTRIAL RESEARCH, New Delhi (IN)

(72) Inventors: Chennur Radhakrishna Reddy, Bhavnagar (IN); Ravi Singh Baghel, Bhavnagar (IN); Nitin Trivedi, Bhavnagar (IN); Puja Kumari, Bhavnagar (IN); Vishal Gupta, Bhavnagar (IN); Kamlesh Prasad, Bhavnagar (IN); Ramavatar Meena, Bhavnagar (IN)

(73) Assignee: Council of Scientific & Industrial Research, New Delhi (IN)

( * ) Notice: Subject to any disclaimer, the term of this patent is extended or adjusted under 35 U.S.C. 154(b) by 65 days.

(21) Appl. No.: 15/109,232

(22) PCT Filed: Dec. 30, 2014

(86) PCT No.: PCT/IN2014/000805
§ 371 (c)(1),
(2) Date: Jun. 30, 2016

(87) PCT Pub. No.: WO2015/102021
PCT Pub. Date: Jul. 9, 2015

(65) Prior Publication Data
US 2016/0355610 A1    Dec. 8, 2016

(30) Foreign Application Priority Data

Dec. 30, 2013    (IN) ........................... 3811/DEL/2013

(51) Int. Cl.
*C12P 19/14* (2006.01)
*C12P 1/00* (2006.01)
(Continued)

(52) U.S. Cl.
CPC ...... *C08B 37/0003* (2013.01); *C08B 37/0039* (2013.01); *C08B 37/0042* (2013.01);
(Continued)

(58) Field of Classification Search
None
See application file for complete search history.

(56) References Cited

U.S. PATENT DOCUMENTS

| 5,801,240 A | 9/1998 | Rideout et al. |
| 6,893,479 B2 | 5/2005 | Eswaran et al. |
| 2013/0005009 A1 | 1/2013 | Mody et al. |

FOREIGN PATENT DOCUMENTS

WO    WO2010/017346 A2    2/2010

OTHER PUBLICATIONS

Harris J. Bixler et al., "A decade of change in the seaweed kydrocolloids industry", J Appl Phycol (2011) 23:321-335.
(Continued)

*Primary Examiner* — Thomas J. Visone
(74) *Attorney, Agent, or Firm* — Patterson Thuente Pedersen, P.A.

(57) ABSTRACT

An integrated process for the recovery of a spectrum of commercially valuable products such as agar, cellulose, lipids, pigments and a liquid rich in minerals of agricultural importance directly from fresh seaweed without employing any catalyst driven in situ chemical conversions. Also solvents used during lipid extraction were shown to be used for three cycles without affecting the yield and quality of successive products. Furthermore, this new process is highly
(Continued)

efficient and utilizes total seaweed raw material without any leftover biomass as solid waste.

14 Claims, 5 Drawing Sheets

(51) Int. Cl.
    *C08B 37/00*     (2006.01)
    *C13K 1/02*     (2006.01)
    *C12P 19/04*     (2006.01)
    *C12P 7/64*     (2006.01)
    *C11B 1/10*     (2006.01)
    *C12P 7/06*     (2006.01)

(52) U.S. Cl.
    CPC ............... *C11B 1/10* (2013.01); *C12P 7/065* (2013.01); *C12P 7/6463* (2013.01); *C12P 19/04* (2013.01); *C12P 19/14* (2013.01); *C13K 1/02* (2013.01); *Y02E 50/17* (2013.01); *Y02P 20/125* (2015.11)

(56) References Cited

OTHER PUBLICATIONS

Puja Kumari et al., "Fatty acid profiling of tropical marine macroalgae: An analysis from chemotaxonomic and nutritional perspectives" Phytochemistry, 2012, 13 pages.
Ratih Pangestuti et al., "Biological activities and health benefit effects of natural pigments derived from marine algae", Journal of Functional Foods 3 (2011) 255-266.
Gaurav Kumar et al., Effect of seaweed liquid extract on growth and yield of *Triticuin aestivum* var. Pusa Gold, J Appl Phycol (2011) 23:251-255.
Ramavatar Meena et al., "Preparation of superior quality products from two Indian agarophytes", J Appl Phycol (2011) 23:183-189.
Ramavatar Meena et al., Preparation, characterization and benchmarking of agarose from *Gracilaria dura* of Indian waters, Carbohydrate Polymers 69 (2007) 179-188.
Kamalesh Prasad et al., "Superior quality agar from red alga *Gelidiella acerosa* (Rhodophyta, Gelidiales) from Gujarat coast of India: An evaluation", Indian Journal of Marine Sciences, vol. 35 (3), Sep. 2006, pp. 268-274.
Kamalesh Prasad et al., "Agars of *Gelidiella acerosa* of west and southeast coasts of India", Bioresource Technology 98 (2007) 1907-1915.
Mahendra K. Shukla, "Partial characterization of sulfohydrolase from Gracilaria dura and evaluation of its potential application in improvement of the agar quality", Carbohydrate Polymers 85 (2011) 157-163.
E. Marinho-Soriano, "Agar polysaccharides from *Gracilaria* species (Rhodophyta, Gracilariaceae", Journal of Biotechnology 89 (2001) 81-84.
Albert Mihranyan et al., "Moisture sorption by cellulose powders of varying crystallinity", International Publication of Pharmaceutics 269 (2004) 433-442.

A.K. Siddhanta, "Profiling of cellulose content in Indian seaweed species", Bioresource Technology 100 (2009) 6669-6673.
E.G. Bligh et al, "A Rapid Method of Total Lipid Extraction and Purification", Canadian Journal of Biochemistry and Physiology, vol. 37, Aug. 1959, No. 8, pp. 911-917.
Priya Sampath-Wiley et al., An improved method for estimating R-phycoerythrin and R-phycocyanin contents from crude aqueous extracts of *Porphyra* (Bangiales, Rhodophyta), J Appl Phycol (2007) 19:123-129.
Savindra Kumar et al., "Bioethanol production from *Gracilaria verrucosa*,a red alga, in a biorefinery approach", Bioresource Technology 135 (2013) 150-156.
D. Mondal et al., "Fuel intermediates, agricultural nutrients and pure water from *Kappaphycus alvarezii* seaweed", RSC Advances, 2013, 3, 17989-17997.
Ravi S. Baghel, "Characterization of agarophytic seasweeds from the biorefinery context", Bioresource Technology 159 (2014) 280-285.
PCT International Search Report for PCT/IN2014/002074, dated May 7, 2015, 5 pages.
PCT Written Opinion of the International Searching Authority for PCT/IN2014/002074, dated May 7, 2015, 7 pages.
Baghel Ravi S et al: "Characterization of agarophytic seaweeds from the biorefinery context", Bioresource Technology, vol. 159, Mar. 3, 2014 (Mar. 3, 2014), pp. 280-285, XP028646292, ISSN: 0960-8524, DOI: 10.1016/J.BIORTECH.2014.02.083.
Francesca M. Kerton et al: "Green chemistry and the ocean-based biorefinery", Green Chemistry, vol. 15, No. 4, Mar. 12, 2013 (Mar. 12, 2013), p. 860, XP055182628, ISSN: 1463-9262, DOI: 10.1039/c3gc36994c.
Albert Mihranyan et al: "Moisture sorption by cellulose powders of varying crystallinity", International Journal of Pharmaceutics, vol. 269, No. 2, 2004, pp. 433-442, XP055182458, ISSN: 0378-5173, DOI: 10.1016/j.ijpharm.2003.09.030.
Kumar Savinora et al: "Bioethanol production from*Gracilaria verrucosa*, a red alga, in a biorefinery approach", Bioresource Technology, Elsevier BV, GB, vol. 135, Nov. 2, 2012 (Nov. 2, 2012), pp. 150-156, XP028579636, ISSN: 0960-8524, DOI: 10.1016/J.BIORTECH.2012.10.120.
Harris J Bixler et al: "A decade of change in the seaweed hydrocolloids industry", Journal of Applied Phycology, Kluwer Academic Publishers, DO, vol. 23, No. 3, May 22, 2010 (May 22, 2010), pp. 321-335, XP019914081, ISSN: 1573-5176, DOI: 10.1007/S10811-010-9529-3.
Ratih Pangestuti et al: "Biological activities and health benefit effects of natural pigments derived from marine algae", Journal of Functional Foods, Elsevier BV, NL, vol. 3, No. 4, Jul. 5, 2011 (Jul. 5, 2011), pp. 256-266, XP028279895, ISSN: 1756-4646, DOI: 10.1016/J.JFF.2011.07.001 [retrieved on Jul. 8, 2011].
Ravi S. Baghel et al: "Biorefining of marine macroalgal biomass for production of biofuel and commodity chemicals", Green Chemistry, vol. 17, No. 4, Jan. 28, 2015 (Jan. 28, 2015), pp. 2436-2443, XP055182530, ISSN: 1463-9262, DOI: 10.1039/C4GC02532F.
Van Hal Jaap W et al: "Opportunities and challenges for seaweed in the biobased economy", Trends in Biotechnology, vol. 32, No. 5, Apr. 22, 2014 (Apr. 22, 2014), pp. 231-233, XP028638855, ISSN: 0167-7799, DOI: 10.1016/J.TIBTECH.2014.02.007.

INTEGRATED PROCESS TO RECOVER A SPECTRUM OF BIOPRODUCTS FROM FRESH SEAWEEDS

RELATED APPLICATIONS

The present application is a National Phase entry of PCT Application No. PCT/IN2014/002074, filed Dec. 30, 2014, which claims priority from IN Patent Application No. 3811/DEL/2013, filed Dec. 30, 2013, said applications being hereby incorporated by reference herein in their entireties.

FIELD OF THE INVENTION

The present invention relates to an integrated process for the complete utilization of fresh seaweed biomass so as to recover a spectrum of bio-products such as natural colorants, total lipids, phycocolloids (agar & refined carrageenan), liquid rich in minerals of agricultural importance and cellulose therefrom. The process ensures complete utilization of raw materials without any leftover solid waste. Furthermore, the solvents utilized during lipid extraction were shown to be reusable for two to three cycles without compromising on the yield and quality of successive products.

BACKGROUND OF THE INVENTION

Seaweeds harvested from both cultivated farms and wild stocks are primarily used as human food particularly in Asian countries such as Japan, China and Korea. Seaweeds are also used as a source for production of phycocolloids, phytosupplements (soil additives, fertilizers), pharmaceuticals, nutraceuticals and cosmetics. Phycocolloids, with global market value over USD 1 billion are the second major commercial product extracted from seaweeds after edible seaweed market.

Bixler and Porse in the article entitled "*A Decade of Change in the Seaweed Hydrocolloids Industry*", *J. Appl. Phycol.* 23, 321-335 (2011) presented a detailed account on production of hydrocolloids (agar, alginates and carrageenan) and trade value from 1999-2009 by world seaweed industry and estimated that production in 2009 was 86,100 dry tons and value as over USD 1.0 billion. All these seaweed industries used whole dry biomass as raw material for extraction of hydrocolloids alone and the leftover solid waste remaining after extraction was used for agricultural applications.

Recently Kumari et al. in *Fatty acid profiling of Tropical Marine Macroalgae: An Analysis from Chemotaxonomic and Nutritional Perspectives, Phytochemistry,* 86, 44-56 (2013) analyzed a wide range of tropical seaweeds for fatty acids and reported occurrence of good amounts of polyunsaturated fatty acids (PUFAs), and further suggested their possible supplementation in nutraceuticals and foods. This study exclusively dealt with fatty acids analysis from the perspective of taxonomy and nutritional value alone and did not report analysis and extraction of other components present in the biomass.

Pangestuti and Kim in *Biological activities and health benefit effects of natural pigments derived from marine algae, J. Funct. Foods.* 3: 255-266 (2011) presented a great deal of information on health beneficiating effects of functional ingredients particularly pigments from marine algal sources. This article exclusively focused on biological activities of marine algae-derived natural pigments and emphasized their potential applications in foods as well as pharmaceutical areas but did not make any attempt to report extraction of other products extracted in the present invention.

Kumar and Sahoo in *Effect of seaweed liquid extract on growth and yield of Triticum aestivum var. Pusa Gold, J. Appl. Phycol.* 23: 251-255 (2011) demonstrated beneficial effects of foliar spray of seaweed liquid extract from brown seaweed *Sargassum wightii* on growth and yields of rice variety Pusa Gold. This article also describes the preparation of seaweed liquid extract but did not report extraction of other products from the seaweed as mentioned in the present invention.

Meena et al. in *Preparation of superior quality products from two Indian agarophytes, J. Appl. Phycol.* 23: 183-189 (2011) described a method for recovery of superior quality agar having gel strength from 250 to 2000±50 g cm$^{-2}$ form *Gelidiella acerosa* and *Gelidium pussillum* of Indian waters following pretreatment of sample with acid and alkali. However, native agars obtained from the above seaweeds without alkali pretreatment yielded gel strength in the range of 250 to 800±25 g cm$^{-2}$. The drawback of their process is 1) pretreatment of sample with acid and alkali and 2) the entire biomass was processed for production of agar alone and not for other bioproducts as described in the present invention.

Meena et al. in *Preparation, characterization and benchmarking of agarose from Gracilaria dura of Indian waters, Carbohyd. Polym.* 69: 179-188 (2007), reported a low gel strength native agar (270±10.84 g cm$^{-2}$) from *G. dura* without alkali pretreatment. However, they subsequently prepared a superior quality agarose from the same seaweed by alkali pretreatment of sample which in turn resulted in increase of gel strength ranging from 280 to 2200 g/cm$^2$. However, this study also describes a process aimed at the recovery of only a single product from feedstock ignoring other ingredients of commercial value.

Prasad et al. in *Superior quality agar from red alga Gelidiella acerosa (Gelidiales Rhodophyta) from Gujarat coast of India: An evaluation, Indian J. Mar. Sci.* 35: 268-274 (2006), disclose a process for preparation of agar having gel strength in the range of 200 to 700 g cm$^{-2}$ from a red seaweed *G. acerosa* from west coast of India. However, their process employed an acid pretreatment of sample, thus yielding a low quality agar in terms of gel strength in contrast to the present invention.

Prasad et al. in *Agars of Gelidiella acerosa of west and southeast coasts of India, Bioresour. Technol,* 98: 1907-1915 (2007) reported the preparation of agar with gel strength ranging from 450 to 845 g cm$^{-2}$ form *G. acerosa* from west coast of India. However, this process also used an acid pretreatment and obtained single product despite having possibilities to produce multiple products from feedstock.

Shukla et al. in *Partial characterization of sulfohydrolase from G. dura and evaluation of its potential application in improvement of the agar quality, Carbohyd. Polym.* 85: 157-163 (2011), disclose the enhancement of commercial agar gel strength to 486 g cm$^{-2}$ from 190 g cm$^{-2}$ by the in situ catalytic application of sulfohydrolase. However, the gel strength was still lower than that achieved in the present invention.

E. Marinho-Soriano in *Agar polysaccharides from Gracilaria species* (Rhodophyta, Gracilariaceae), *J. Biotechnol.* 89: 81-84 (2001) described extraction of agar polysaccharides from different species of *Gracilaria* (Rhodophyta, Gracilariaceae) including *Gracilaria dura*, using hot water extraction at 110 degree C. for 1 hr, without any pretreatment of the seaweed. The gel strength of *G. dura* agar was 318 g cm$^{-2}$. However, this method also deals with extraction of a single product from feedstock despite having possibilities to prepare multiple products.

Mihranyan et al. in *Moisture sorption by cellulose powders of varying crystallinity, Int. J. Pharm.* 269: 433-442 (2004), disclosed the method for cellulose extraction. However, the major drawback of this process is the defatting of biomass prior to cellulose extraction, and prolonged process duration.

Siddhanta et al. in Profiling of cellulose content in Indian seaweed species, *Bioresour. Technol.* 100: 6669-6673 (2009), reported the cellulose contents of several seaweeds from Indian water. However, the cellulose profiling method included defatting of biomass prior to cellulose extraction, use of excessive chemicals and time consuming.

Bligh et al. in *A rapid method of total lipid extraction and purification, Can. J. Biochem. Phys.* 37(8):911-915, (1959), disclosed a method for the extraction of only lipids from biomass and made no effort to isolate other ingredients from biomass.

Sampath-Wiley et al. in *An improved method for estimating R-phyoerythrin and R-phycocyanin contents from crude aqueous extracts of Porphyra* (Bangiales, Rhodophyta), *J. Appl. Phycol.* 19:123-129 (2007), described the method for the extraction and estimation of pigments in the red seaweed *Porphyra* sp. However, they did not report the extraction of other products as described in the present invention.

Kumar et al. in *Bioethanol production from Gracilaria verrucosa, a red alga, in a biorefinery approach, Bioresour. Technol*, 135:150-156 (2013), successfully demonstrated agar and bioethanol production from algal waste (rich in holocellulose) that remained after agar extraction from *Gracilaria verrucosa* (Hudson) Papenfuss. However, this process deals with production of two products only and also used dry biomass preventing realization of other products.

Mondal et al. in Fuel intermediates, agricultural nutrients and pure water from *Kappaphycus alvarezii* seaweed, *RSC Advances.* 3:17989-17997 (2013), described an integrated method for the preparation of fuel intermediates, agricultural nutrients and pure water from the red seaweed *Kappaphycus alvarezii*. However, in this process extensive in situ chemical conversions aided by catalysts from external sources were employed for achieving satisfactory yield and quality of products, whereas the present invention does not include any external catalysts.

Rideout et al. in U.S. Pat. No. 5,801,240 reported the method for extracting the semi refined carrageenan from seaweed. However, the process was specific to recover a single product. The present invention on the other hand describes the process for the recovery of refined carrageenan along with the several byproducts such as natural pigments, lipid, minerals and bioethanol from fresh seaweed biomass.

Eswaran et al. in U.S. Pat. No. 6,893,479 described an integrated method for production of carrageenan and liquid fertilizer from fresh seaweeds. However, the limitation of this process is that it provides only two products from fresh biomass as initial starting material ignoring the rest of the spectrum of products as isolated in the present invention.

Mody et al. in Patent US 2013/0005009, described a process for integrated production of ethanol and seaweed sap from *Kappaphycus alverezii*. This process also demonstrated recovery of maximum of two products only from feedstock. The major drawbacks of this process was that the carrageenan fraction was targeted for bioethanol production which is an important marketable polysaccharide and the process also includes acid treatment for hydrolysis as contrary to the present invention.

Baghel et al. in *Characterization of agarophytic seaweeds from the biorefinery context, Bioresour. Technol*, 159: 280-285 (2014) reported quantification of various components of biomass such as natural colorants (R-phycoerythrin (R-PE), R-phycocyanin (R-PC)), minerals, proteins, lipids, cellulose and agar in a range of red seaweeds and suggested their possible extraction in order to develop seaweed biorefinery, however authors did not report any scheme or process useful for biorefinery.

In short, it may be summarized that most of the processing technologies developed so far for recovering valuable products from seaweeds are aimed at extracting only one or two products at a time as well as utilize chemical conversions through catalytic routes for transformation of various natural products into high value products.

Thus, keeping in view the drawbacks of the hitherto reported prior art, the inventors of the present invention realized that there exists a dire need to provide a holistic approach to derive a spectrum of bioproducts such as natural colorants, total lipids, phycocolloids, cellulose and nutrient rich liquid product of commercial value from fresh seaweeds, wherein the process ensures complete utilization of raw materials without leftover solid waste, while simultaneously reusing the solvents utilized for two to three successive cycles without compromising on the quality of the successive products.

SUMMARY OF THE INVENTION

The main objective of the present invention is thus to develop a systemic process that utilizes the total seaweed biomass for production of a spectrum of bio-products such as natural colorants, total lipids, agar, cellulose and nutrient rich liquid product having high commercial value.

Another objective of the present invention is to produce bioethanol from the cellulose recovered in the integrated process as feedstock. Yet another objective is to reuse the organic solvents used in lipid extraction for subsequent extraction processes and test the lipid yields obtained using the recycled solvent. Still another objective is to compare the yields and quality of co-generated products obtained from this process with those obtained individually from the processing of primary biomass following conventional processes. Yet another objective is to compare the physicochemical properties of agar produced from this method with those obtained individually from the processing of primary biomass following conventional processes.

Still another objective is to test the suitability of phycocolloid (agar) extracted from this process for its microbiological application.

Yet another objective is to establish the scope of feasibility of this integrated process for other seaweeds.

Still another objective is to minimize the usage of chemicals in the integrated process.

Yet another objective is the complete utilization of algal biomass without leaving any waste.

The present invention relates to the development of an integrated process for recovery of a spectrum of commercially valuable bioproducts such as natural colorants, total lipids, phycocolloids, nutrient rich liquid product and energy dense cellulose from fresh seaweeds. Further, the isolated cellulose is targeted for bioethanol production. The feasibility of the developed method was further confirmed by experimenting with four more red seaweeds such as *Gracilaria dura, Gelidium pusillum, Kappaphycus alvarezii* and *Sarconema scinaioides*.

The various components contained in seaweeds such as pigments, proteins, carbohydrates, minerals, lipids, cell wall polysaccharides etc. are immensely useful in food, pharmaceutical, agrochemical, nutraceutical, industrial and personal care products, if extracted without affecting their yield and quality. The seaweed markets worldwide are growing steadily and have an estimated market value of over USD 7.0 billion per annum. Till date the processing technologies developed for recovering the said valuable products from seaweeds are designed to extract only one or two products and use chemical conversions through catalytic routes for transformation of various natural products into high value end products.

The present invention discloses a holistic approach to derive a spectrum of bioproducts such as natural colorants, total lipids, phycocolloids, cellulose and liquid rich in minerals of agricultural importance from fresh seaweeds. The yield and quality of products obtained via the present process is quite comparable with those obtained individually from the same source. It is noteworthy that the recovery of natural products one after the other resulted in increased gel strength of the recovered agar (546 to 1240 $g/cm^2$) as compared to that obtained from the same source individually (250 to 750 $g/cm^2$). Further, the process ensures complete utilization of raw materials without any leftover solid waste. Furthermore, the solvents utilized during lipid extraction were shown to be reusable for two to three cycles without compromising on the yield and quality of successive products.

DETAILED DESCRIPTION OF THE INVENTION

Figure 1:
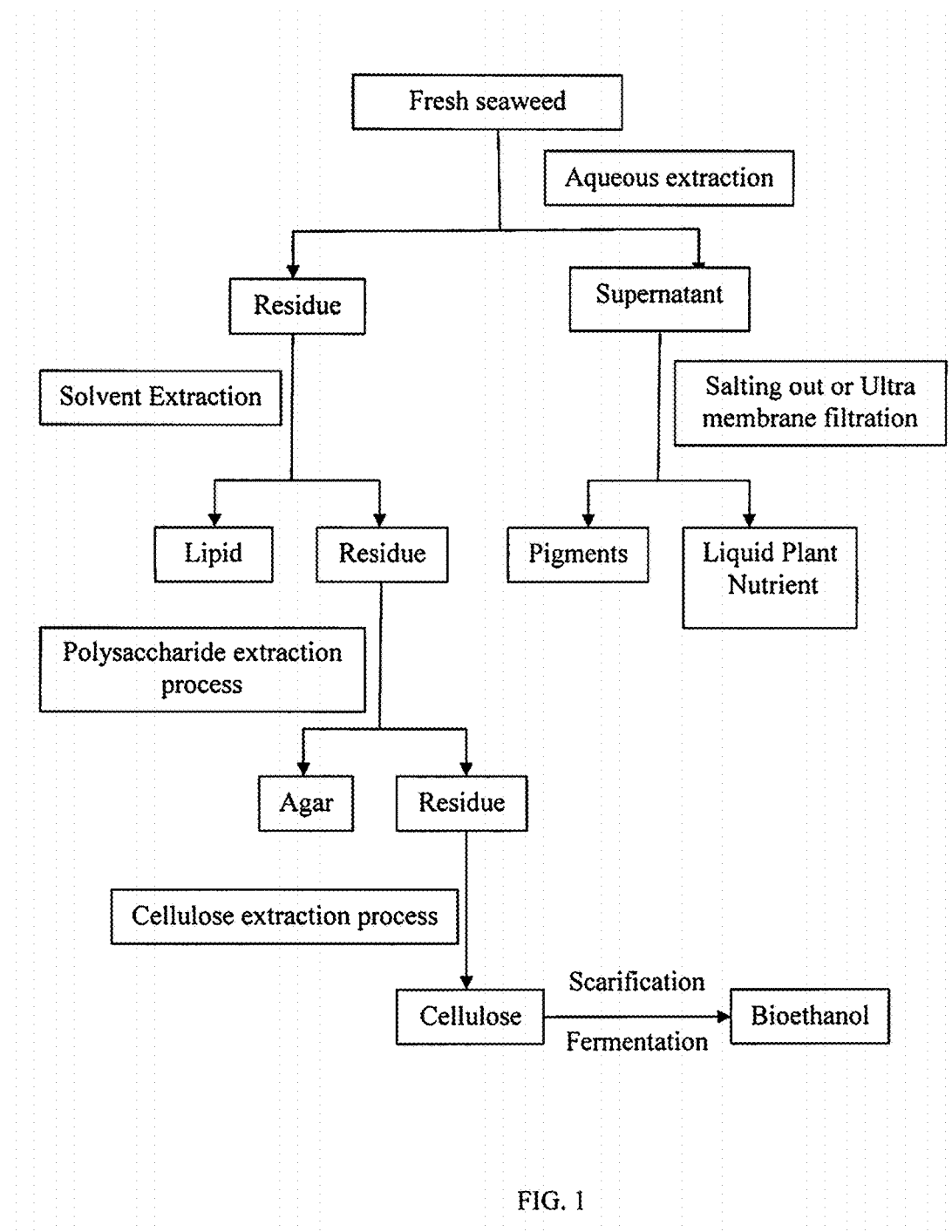
FIG. 1 illustrates the complete process for the recovery of bioproducts from seaweed biomass.

Most of the seaweed processing technologies published in literature report the recovery of maximum two or three products therefrom. The most recent process has indeed described the realization of multiple products such as fuel intermediates, agricultural nutrients and pure water from red seaweed *Kappaphycus alvarezii*. In this process extensive in situ chemical conversions aided by catalysts from external sources were employed for achieving satisfactory yield and quality of products. However, in the present invention, the major seaweed natural products such as agar, cellulose, lipids, pigments and a liquid rich in minerals of agricultural importance were directly recovered from fresh seaweed without employing any catalyst driven in situ chemical conversions. Also, the solvents used during lipid extraction were shown to be used for three cycles without affecting the yield and quality of successive products. Furthermore, this new process is highly efficient and utilizes total seaweed raw material without any leftover biomass as solid waste.

This new invented process virtually demonstrates the means and order of recovery of a spectrum of bioproducts in their totality in an integrated manner from fresh seaweeds. Most of the bioproducts obtained through this process are primary products and can be further functionalized aiming at speciality applications using catalyst driven chemical conversion routes.

The previous investigations have mostly focused on the development of sustainable extraction methods for industrial scale production of phycocolloids such as agar, alginates and carrageenan alone from seaweeds, despite the availability of various other natural products of high commercial value therewith. It is in this context, an attempt was made to develop an innovative process aimed at recovering a spectrum of bioproducts in an integrated manner from fresh seaweeds. The quality and yield of products obtained from the present process is sometimes superior, particularly in case of agar and carrageenanthan those of the individual products obtained from seaweed biomass following conventional practices.

Fresh seaweeds used for the purposes of the present invention were collected from following Indian coasts

| Sl. No. | Name of the Seaweed | Complete postal address of the place including the PIN CODE from where the fresh seaweed was Collected |
|---|---|---|
| 1 | *Gracilaria dura* | Veraval Coast, Post Office Veraval Rayon Factory (Sub Office), Junagadh, Gujarat, India, Pin Code:- 362266. Adri Coast, Post Office Adri (Branch Office), Junagadh, Gujarat, India, Pin Code:- 362255 |
| 2 | *Gelidiella acerosa* | Veraval Coast, Post Office Veraval Rayon Factory (Sub Office), Junagadh, Gujarat, India, Pin Code:- 362266. Adri Coast, Post Office Adri (Branch Office), Junagadh, Gujarat, India, Pin Code:- 362255 |
| 3 | *Gellidium pusillum* | Valinokkam Coast, Post Office Valinokkam (Branch Office), Ramanathapuram, Tamil Nadu, India, Pin Code:- 623528 |
| 4 | *Kappaphycus alvarezii* | Okha Coast, Post Office Okha (Sub Office), Jamnagar, Gujarat, India, Pin Code:- 361350 |
| 5 | *Sarconema scinaioides* | Veraval Coast, Post Office Veraval Rayon Factory (Sub Office), Junagadh, Gujarat, India, Pin Code:- 362266. |

The culture *Saccharomyces cerevisiae*, as used for the purposes of the present invention was commercially procured from MTCC, Institute of Microbial Technology, Chandigarh, India vide number MTCC No. 180. The *Escherichia coli*, as used for the purposes of the present invention was revived from EZ competent cells procured from Qiazen Cat. No. 231222.

Seaweeds are known to contain a variety of products such as pigments, proteins, carbohydrates, minerals, lipids, cell wall polysaccharides etc. in various proportions depending on the species and the season of growth. All these products have been used as ingredients in diverse food, pharmaceutical, agrochemical, nutraceutical, industrial and personal care products, and have well established international and national markets. The seaweed markets worldwide are growing steadily and have an estimated market value over USD 7.4 billion per annum. Most of the processing technologies developed so far for seaweeds are aimed at extraction of one or mostly two products and use chemical conversions through catalytic routes for transformation of various natural products into high value products.

Figure 2:
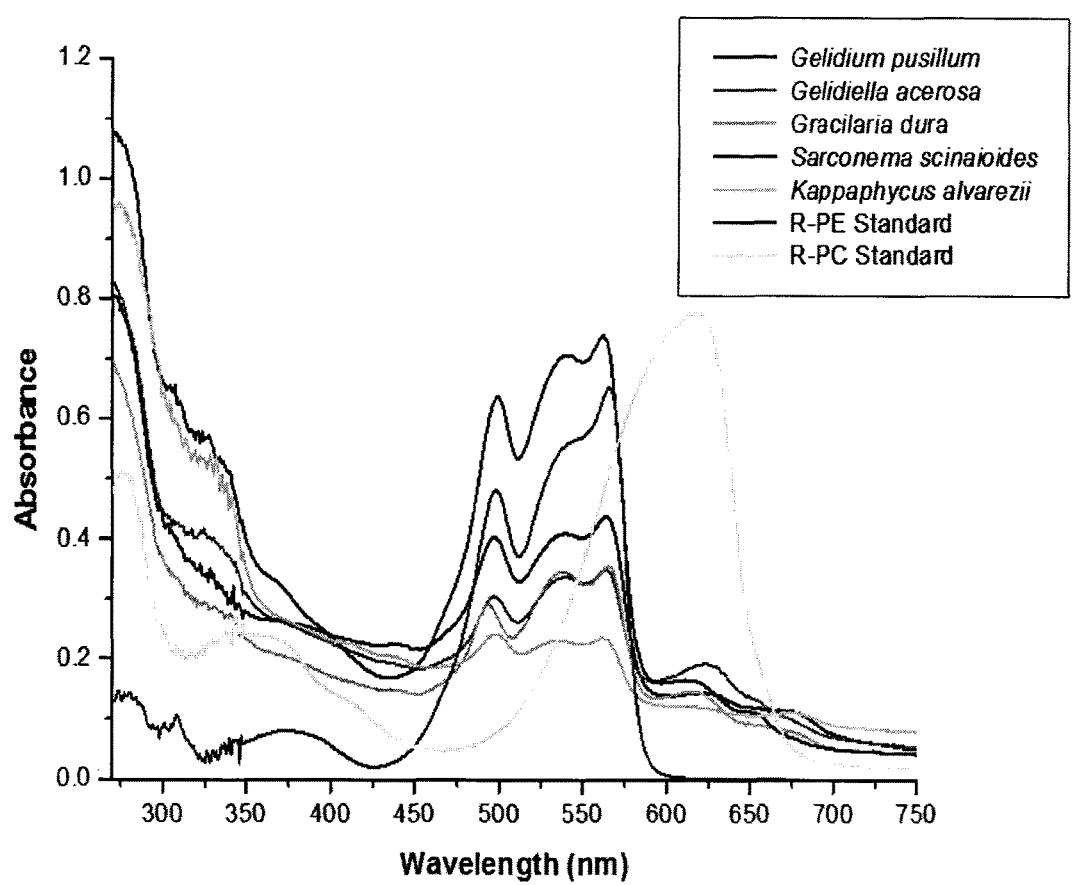
FIG. 2 depicts the UV-spectra of pigment standards of R-Phycoerythrin (R-PE) and R-Phycocyanin (R-PC) and extracted pigments from different seaweeds.

The present invention provides a process that enables the recovery of a spectrum of bioproducts of commercial importance in an integrated manner along with bioethanol from fresh seaweeds. The complete process for the recovery of bioproducts from seaweed biomass is illustrated in FIG. 1. The steps comprising the said integrated process developed in the present invention are given here as under:

1. 50 g of fresh seaweed sample was homogenized in 100 ml chilled 0.1M phosphate buffer (pH 6.8) using a mixer grinder and incubated for 12 hrs at 4 degree C. Following the incubation, the contents in the phosphate buffer were mixed thoroughly and centrifuged at 7000 rpm at 4 degree C. for 15 minute. The supernatant containing crude pigment was collected and the traces of pigments remaining in the residual mass were further recovered by repeating extraction in 50 ml phosphate buffer without incubation. The supernatants as collected were mixed and purified.
2. Purification of pigments were carried out by precipitation with 10, 20, 30 40 and 50% of ammonium sulfate. The pellet containing pigment was dissolved in phosphate buffer. R-phycoerythrine [R-PE] and R-phycocyanine [R-PC] pigment content was quantified using spectrophotometric method. The absorbance was measured with double beam UV-Vis spectrophotometer (UV-160, Shmadzu, Japan) at 280, 564, 618 and 730 nm (FIG. 2). The concentration of pigments R-PE and R-PC were calculated according to equation given by Sampath-Wiley et al. (2007):

$R\text{-}PC = 0.154(A_{618} - A_{730})$ $R\text{-}PE = 0.1247((A_{564} - A_{730}) - 0.4583(A_{618} - A_{730}))$ 3. 30% concentration of ammonium sulfate was found to be optimal for maximum yield of pigments maintaining the highest purity index for agarophytic seaweeds while 40% was the concentration for carragenophytes. The supernatant obtained after precipitation of pigments were analyzed for mineral composition using Inductive Coupled Plasma (ICP) spectroscopy.
4. Residue obtained following the pigment extraction was then used for recovery of total lipid. The total lipids were extracted with chloroform and methanol (1:2 v/v). Both the aqueous and greenish organic layers were collected separately. The organic extract was filtered and washed with water and dried using rotary evaporator. The lipid yields were measured gravimetrically.
5. Residue leftover after lipid extraction was kept at 65 degree C. for 1 h to remove remaining solvents and used for agar extraction if the primary seaweed was an agarophyte. 1:5 (w/v of initial fresh algal biomass) volume of distilled water was added to residue and cooked at 120 degree C. for 1.5 hrs in autoclave. The cooked materials were homogenized immediately using mixer grinder and centrifuged at 7000 rpm for 6 minute at hot condition. The supernatant was collected and left for gel formation at room temperature. The gelled material was frozen in the freezer at −20 degree C. for 15 h and thawed to obtain the native agar. Agar obtained after thawing was dried at 65 degree C. for 12 hrs.
6. Residue leftover after lipid extraction was kept at 65 degree C. for 1 h to remove remaining solvents and used for carrageenan extraction if the primary seaweed was a carragenophyte. The residue was treated with 8% KOH and cooked at 72° C. for 2 hrs.

Following the cooking, the content was filtered through muslin cloth. The leftover material was washed with tap water till neutrality then added 100 ml water and cooked at 78 degree C. for 45 minutes. The cooked material were homogenized well and centrifuged at 7000 rpm for 3 minutes. The supernatant was collected and precipitated in chilled iso-propanol (1:2 v/v). Precipitate was dried at 60° C. for 4 hrs. The residual mass obtained from centrifugation was used for cellulose extraction.

Figure 3:
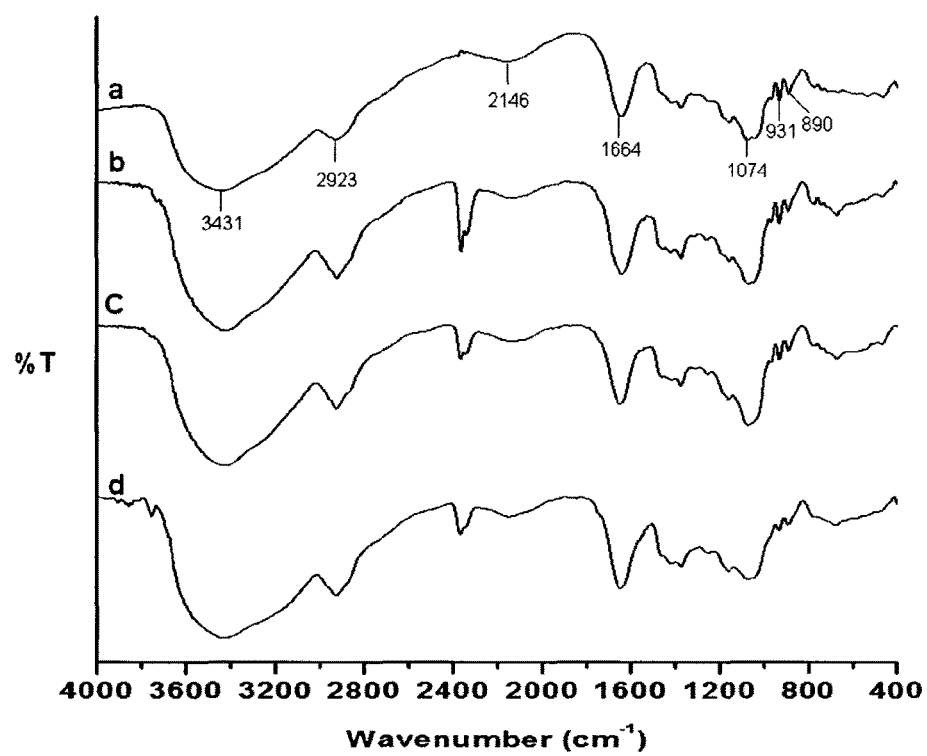
FIG. 3 elucidates the comparison of FTIR spectra of agar of (a) commercial standard bacto agar, and agars extracted from (b) *Gelidium pusillum* (c) *Gelidiella acerosa* (d) *Gracilaria dura* following integrated process.
Figure 4:
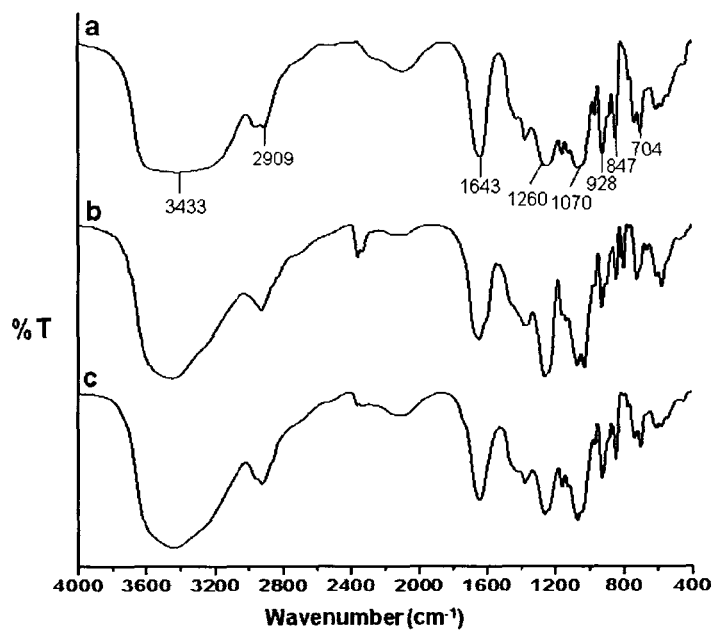
FIG. 4 depicts the comparison of FT-IR spectra of carrageenan of (a) κ-carrageenan (Sigma-Aldrich) and carrageenan extracted from (b) *Sarconema scinaioides*, (c) *Kappaphycus alvarezii* following integrated process.
Figure 5:
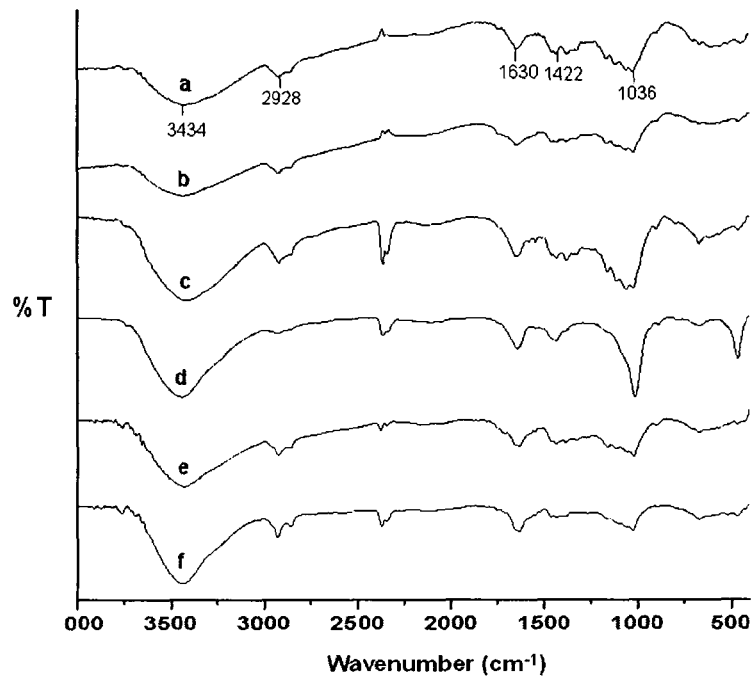
FIG. 5 reveals the comparison of FTIR spectra of cellulose of (a) Whatman filter paper and cellulose extracted from (b) *Sarconema scinaioides* (c) *Kappaphycus alvarezii* and (d) *Gelidium pusillum* (e) *Gelidiella acerosa* (f) *Gracilaria dura* following integrated process.

7. The residual mass that remained after agar or carrageenan extractions was used for cellulose extraction. Residual pulp was soaked in acetate buffer containing 36% $NaClO_2$ (w/w) for bleaching at 60 degree C. for 8 hrs. The bleached material was washed with water to get neutralized algal biomass. Thereafter, it was treated with 0.5 M NaOH solution at 60 degree C. for 12 hrs. The alkali treated mass was then washed with water till neutrality. The neutralized biomass was then separated and dried at room temperature. The dried residue obtained was re-suspended in 5% v/v hydrochloric acid and heated up to boiling. The resultant slurry was kept overnight at room temperature, followed by washing with water to remove the excess acid and dried to obtain cellulose.
8. Agar, carrageenan and cellulose were characterized using instrument Fourier transforms infrared (FT-IR) Perkin-Elmer Spectrum GX FTIR (USA) and spectra matched with commercial products (FIG. 2; FIG. 3 & FIG. 4)
9. The gel strength of extracted agar samples was measured using a Nikkansui gel tester (Kiya Seisakusho, Tokyo, Japan). For the determination of gel strength, 1.5% agar solution was prepared in milli Q water and kept at 10 degree C. for 12 h. The measurement was performed at 20 degree C. The gelling and melting temperatures were measured according to the method described by Shukla et al. [Carbohydrate Polymers. 2011, 85: 157-163].
10. The gel strength of extracted carrageenan sample was measured by using a Nikkansui gel tester (Kiya Seisakusho, Tokyo, Japan). For the determination of gel strength, 1% carrageenan solution was prepared in 1% KCl and kept at 10 degree C. for 12 h. The measurement was performed at 20 degree C.

In order to compare the yield of products obtained through the developed integrated process with those obtained individually from primary biomass, agar, lipid and cellulose was extracted from primary biomass following the methods of Meena et al. [Journal of Applied Phycology. 2008, 23(2): 183-189], Bligh and Dyer [Canadian Journal of Biochemistry and Biophysiology. 1959, 37(8): 911-915] and Mihranyan et al. [International Journal of Pharmaceutics. 2004, 269: 433-442], respectively.

To further confirm the consistency and reproducibility of findings of the present integrated process, additional small scale trials utilizing 500 g of *G. acerosa* biomass were carried out. The yield and properties of products obtained with small scale trials were found to be comparable with those obtained with 50 g biomass.

In an embodiment, the present invention provides a holistic approach to recover a spectrum of bioproducts of commercial value by utilizing the total biomass leaving no residual solid waste.

In another embodiment, the present invention provides a process that has the possible reusability of solvents used for lipid extraction. The solvents used for lipid extraction were recovered and used up to three successive cycles without affecting the lipid yields and residual biomass contents.

In yet another embodiment of the present invention, the yield and quality of the products co-generated through this invented process is quite comparable with those obtained individually from the same source of primary biomass (Table 1 & Table 2). Further, the recovery of natural products in sequence has resulted in significant increase in gel strength of agar (Table 1).

In still another embodiment of the present invention, the process ensures total utilization of the raw materials used.

In still another embodiment, the invention relates to agar from *G. acerosa* having the following characteristics:
  i. Gel strength (1.5%): 1240±20 g/cm$^2$
  ii. Gelling temperature: 41±1 degree C.
  iii. Melting temperature: 92.5±0.5 degree C.

In yet another embodiment, the invention relates to agar from *G. pusillum* having the following characteristics:
  i. Gel strength (1.5%): 1150±50 g/cm$^2$
  ii. Gelling temperature: 45±0.5 degree C.
  iii. Melting temperature: 96±0.5 degree C.

In yet another embodiment, the invention relates to agar from *G. dura* having the following physicochemical properties:
  i. Gel strength (1.5%): 546±25 g/cm$^2$
  ii. Gelling temperature: 35±1 degree C.
  iii. Melting temperature: 86.5±0.5 degree C.

In still another embodiment, the invention relates to refined carrageenan from *K. alvarezii* having the following characteristics:
  i. Gel strength: 1040±36 g/cm$^2$ (1% gel in 1% KCl)

In yet another embodiment, the invention relates to refined carrageenan from *Sarconema scinaioides* having gel strength of 100 g/cm$^2$ (1% gel in 1% KCl).

In yet another embodiment of the present invention, pretreatment is not required for agar extraction as opposed to the conventional extraction methods.

In still another embodiment of the present invention, the process enables to produce agar with high gel strength without alkali treatment as conventionally done.

In yet another embodiment of the present invention, the gel strength of the phycocolloid (agar) obtained is superior than that obtained using conventional agar extraction and exhibits 1.5 to 2.9 fold increase in gel strength.

In still another embodiment of the present invention, the agar produced from different species of seaweeds such as *Gelidiella acerosa*, *Gelidium pusillum* and *Gracilaria dura* is suitable for microbiological applications in concentrations equal or lower to that compared with the commercial agar.

In yet another embodiment of the present invention, the produced agar shows gel strength in the range of 500-1200 g/cm$^2$.

In still another embodiment of the present invention, the recovery of multiple products from seaweed biomass sequentially yielded 10-25% left over residue which is used as a feedstock for cellulose extraction.

In yet another embodiment of the present invention, the residual mass minimizes the use of chemicals up to 75 to 90% for cellulose extraction.

In still another embodiment of the present invention, the cellulose is produced without any additional discoloration and defatting as opposed to the conventional methods.

In yet another embodiment of the present invention, the liquid obtained after salting out of the pigment contained high amount of ammonium sulphate in addition to good quantity of seaweeds based macro- and micro-minerals.

In still another embodiment of the present invention, the solvents used during lipid extraction were shown to be reusable for three cycles without compromising on the yield and quality of the successive products.

In a further embodiment of the present invention, an attempt was made to develop an innovative process aimed at recovering a spectrum of a variety of bio-products such as natural colorants (pigments), lipids, liquid rich in minerals, phycocolloid (agar) and cellulose in an integrated manner from fresh seaweed, wherein the main ingenious steps are:
  1. Development of a systemic approach for valorization of seaweed biomass for a spectrum of bioproducts such as pigments, lipids, agar, cellulose and liquid rich in minerals from fresh seaweeds which are of immense commercial value.
  2. The yields of the products obtained through this new process are comparable with those obtained individually.
  3. The gel strength of phycocolloid (agar) obtained through this process was superior and showed 1.5 to 2.9 fold increase than that extracted directly.
  4. The liquid obtained in this new process contained soluble minerals, proteins, phosphate and good quantity of ammonium sulfate which could perhaps serve as an excellent source of biofertilizer for agriculture.
  5. The solvents used during lipid extraction were shown to be reusable for two cycles without compromising on the yield and quality of successive products.
  6. Also, this new process ensures the efficient and total utilization of seaweed raw material for preparation of bioproducts without any leftover biomass as solid waste.

Accordingly, the present invention provides an integrated process to recover a spectrum of bioproducts from fresh seaweeds, wherein the steps comprising:
  [a] homogenizing the fresh seaweeds using mixer grinder in phosphate buffer having pH in the range of 6.8 to 7.0 and incubating at a temperature in the range of 4 to 6 degree C. for a time period of 10 to 12 hours followed by centrifugation at 5000 to 7000 rpm at 4 to 10 degree C. for 12 to 15 minutes and separating the supernatant containing pigments and protein from residual mass;
  [b] precipitating the pigments from supernatant as obtained in step [a] with 30% agarophytes and 40% carrageenophytes of ammonium sulphate followed by centrifugation at 6500 to 8000 rpm at 4 to 10 degree C. for 12 to 15 minutes and dissolving the pelleted pigments in phosphate buffer having pH in the range of 6.8 to 7.0 followed by quantification of the pigments using spectrophotometric method, recording the absorbance using double beam UV-Vis spectrophotometer at 280, 564, 618 and 730 nm and calculating the concentration of pigments R-PE and R-PC according to the equation:

$$R\text{-}PC = 0.154(A_{618} - A_{730})$$

$$R\text{-}PE = 0.1247((A_{564} - A_{730}) - 0.4583(A_{618} - A_{730}));$$

[c] analyzing the composition of supernatant obtained from step [b] for the presence of various plant nutrient including macro and micro minerals using Inductive Coupled Plasma (ICP) spectroscopy;

[d] extracting the total lipids from the residual mass as obtained in step [a] using the solvents chloroform and methanol mixed in a ratio of 1:2 v/v followed by centrifugation at 4000 to 5000 rpm at 4 to 10 degree C. for 10 to 15 minutes and separating the aqueous and greenish organic extract layer from the residual mass;

[e] filtering the organic extract as obtained in step [d] and washing with equal volume of mili Q water followed by drying using rotary evaporator and gravimetric quantification of lipids;

[f] subjecting the residual mass as obtained in step [d] for agar extraction, if the seaweed is an agarophyte by drying it at a temperature in the range of 60 to 65 degree C. for 50 minute to 1 hr followed by cooking with 1:5 w/v (of initial fresh algal biomass) of distilled water at 115 to 120 degree C. for 1 hr 20 minutes to 1.5 hours in an autoclave and homogenizing the cooked material immediately using mixer grinder followed by centrifugation at 6000 to 7000 rpm at 40 to 60 degree C. for 4 to 6 minutes to obtain the supernatant and residual mass;

[g] allowing the supernatant as obtained in step [f] to form a gel at temperature in the range of 25 to 30 degree C. followed by freezing at minus 15 to minus 20 degree C. for 12 to 15 hours and thawing to obtain the native agar which is dried at 60 to 65 degree C. for 10 to 12 hours to obtain the dry agar;

[h] subjecting the residual mass as obtained in step [d] for carrageenan extraction, if the seaweed is a carrageenophyte by drying it at a temperature in the range of 60 to 65 degree C. for 50 minutes to 1 hr followed by cooking with 8% KOH at 70 to 72 degree C. for 1 hr 45 minutes to 2 hours, filtering the contents through muslin cloth and washing the filtrate with tap water till neutrality followed by cooking it with 100 ml water at 75 to 78 degree C. for 40 to 45 minutes;

[i] homogenizing the cooked material as obtained in step [h] and centrifuging at 6000 to 7000 rpm for 3 to 5 minutes to obtain the supernatant and residual mass, precipitating the supernatant in chilled iso-propanol (1:2 v/v) and drying the precipitate at 60 to 65 degree C. for 4 to 6 hours to obtain carrageenan;

[j] characterizing the agar and carrageenan obtained in steps [g] and [i] respectively using Fourier transformation infrared (FT-IR) spectroscopy and measuring the gel strength of agar and carrageenan following standard methods;

[k] drying the residual mass as obtained in steps [f] and [i] and soaking in acetate buffer of pH 4.5 to 5 containing 36% $NaClO_2$ (w/w) for bleaching at 60 to 65 degree C. for 7 to 8 hours, washing of bleached material with water to neutralize it and treating the washed material with 0.5 M NaOH solution at 60 to 65 degree C. for 10 to 12 hours followed by washing with water till neutrality;

[l] drying the neutralized material as obtained in step [k] and treating with 5% v/v of hydrochloric acid followed by heating till boiling, incubating at temperature of 25 to 30 degree C. for 10 to 14 hours and washing the slurry with water till neutrality followed by drying to get cellulose;

[m] hydrolyzing the cellulose as obtained in step [l] with commercial cellulase in sodium acetate buffer of pH 4.8 and incubating for 36 hrs at 45 degree C. on an orbital shaker, measuring the reducing sugar spectrophotometrically using 3,5-dinitrosalisylic acid method;

[n] enriching the hydrolysate as obtained in step [m] with 5 g/L peptone and 3 g/L yeast extract followed by sterilization in an autoclave, inoculating the culture of *Saccharomyces cerevisiae*, and incubating it for 12 hrs at 28±2 degree C. on an orbital shaker to obtain ethanol; analyzing the ethanol yield and residual reducing sugars by GC-MS and DNS method, respectively

EXAMPLES

The following examples are given by way of illustration and therefore should not be construed to limit the scope of the present invention.

Example 1

50 g of washed fresh *Gelidella acerosa* sample was homogenized in 100 ml of 0.1M chilled phosphate buffer (pH 6.8) using mixer grinder and incubated for 12 hrs at 4 degree C. Following the incubation, the contents in phosphate buffer was mixed thoroughly and centrifuged at 7000 rpm at 4 degree C. for 15 minutes. The supernatant containing crude pigment was collected and residual part was further subjected to pigment extraction as above using 50 ml of phosphate buffer. The supernatant fraction with pigments was purified by precipitation with 30% ammonium sulfate for 12 hrs at 4 degree C. and centrifuged at 7000 rpm at 4 degree C. for 20 minutes. The pellet containing pigment was dissolved in phosphate buffer and R-phycoerythrine (R-PE) and R-phycocyanine (R-PC) content were quantified using spectrophotometric method. The absorbance was taken by double beam UV-Vis spectrophotometer at 280, 564, 618 and 730 nm. The concentration of pigments R-PE and R-PC were calculated according to equation given by Sampath-Wiley et al. (2007). The R-PE and R-PC contents were 419±3 and 303±4 µg/g fresh weight basis (FW). 153±3 ml of liquid obtained as supernatant from precipitation of pigments and further analyzed for mineral composition using ICP. Macro and micro minerals composition of liquid extract is presented in Table3.

The residue as obtained following the pigment extraction was then used for recovery of total lipid. The total lipids were extracted with chloroform and methanol (1:2 v/v) followed by centrifugation in 4000 rpm at 4 degree C. for 20 minutes. Both the aqueous and greenish organic layers were collected separately. The process was repeated four times. Organic extract was filtered and washed with equal volume of mili Q water and dried using rotary evaporator. The lipid yield was measured gravimetrically. The lipid yield was 1.41±0.10 on dry weight basis (DW).

Residue leftover from lipid extraction was kept at 65° C. for 1 hr to remove residual solvents and thereafter used as feedstock for agar extraction. 1:5 (w/v) volume of distilled water was added to residue and cooked at 120 degree C. for 1.5 hrs in autoclave. The cooked material was homogenized immediately using mixer grinder and centrifuged at 7000 rpm for 6 minutes at hot condition. The supernatant was collected and left for gel formation at room temperature. The gelled material was frozen in the freezer at −20 degree C. for 15 hrs and thawed to obtain the native agar. The agar was purified twice by freeze thawing. Agar obtained after thawing was dried at 65 degree C. for 12 hrs. Agar yield was 23.24±0.55% (DW) (Table 1), having 1240±20 g/cm$^2$ gel strength (1.5% gel; 20 degree C.), and 41±1 degree C. gelling temperature.

The residual pulp that remained after agar extraction was dried at room temperature and further used for cellulose extraction. Residual pulp was soaked in acetate buffer containing 36% NaClO$_2$ (w/w) for bleaching at 60 degree C. for 8 hrs. The bleached pulp was washed with water to neutralize. Thereafter, the pulp was treated with 0.5 M NaOH solution at 60 degree C. for 12 hrs. The alkali treated pulp was washed with water till neutrality. The neutralized pulp was then separated and dried at room temperature. The dried biomass obtained was re-suspended in 5% v/v hydrochloric acid and heated up to boiling. The resultant slurry was kept overnight at room temperature, followed by washing with water, to remove the excess acid and dried to obtain cellulose. Cellulose yield was 8.84±0.5% (DW) (Table 1). The experiment was performed in triplicates.

Example 2

50 g *Gelidium pusillum* sample was processed for extraction of multiple products in an integrated manner as per example 1. The R-PE and R-PC contents were 715±5 and 99±12 g/g on Fresh weight basis (FW). The supernatant 157±3 ml obtained following the precipitation of pigments was analyzed for mineral composition using ICP. Macro and micro minerals composition of liquid extract is presented in Table 3. The lipid yield was 1.26±0.05 (DW). Agar yields was 24.78±0.94% (DW) (Table 1), having 1150±50 g/cm$^2$ gel strength (1.5% gel; 20 degree C.), and 45±0.5 degree C. gelling temperature. Cellulose yield was 11.01±0.7% (DW). The experiment was performed in triplicates.

Example 3

50 g *Gracilaria dura* sample was processed for extraction of multiple products in an integrated manner as per example 1. The R-PE and R-PC contents were 340±5 and 160±5 g/g on fresh weight basis (FW). The supernatant 180±4 ml obtained following the precipitation of pigments was analyzed for mineral composition using ICP. Macro and micro minerals composition of liquid extract is presented in Table 3. The lipid yield was 0.94±0.05 (DW). Agar yields was 23.24±0.55% (DW) (Table 1), having 546±25 g/cm$^2$ gel strength (1.5% gel; 20 degree C.), and 35±1 degree C. gelling temperature. Cellulose yield was 3.57±0.10% (DW). The experiment was performed in triplicates.

Example 4

50 g *Kappaphycus alvarezii* fresh sample was processed for extraction of multiple products in an integrated manner as in example 1 except the pigment extraction wherein 40% ammonium sulphate was employed to achieve maximum yields, while residue obtained from lipid extraction was used as feedstock for carrageenan. Residual material was treated with 8% KOH for 2 hrs at 72° C. After incubation the material was filtered through muslin cloth. The material was added with 100 ml water and neutralized with HCl, further cooked at 80 degree C. for 45 minutes. The cooked material was homogenized well and centrifuged at 7000 rpm for 3 minutes. The supernatant was collected and precipitated with chilled iso-propanol (1:2 v/v). Precipitate was dried at 65° C. for 4 hrs. The residual mass obtained from centrifugation was used for cellulose extraction as per example 1. The R-PE and R-PC contents were 54±3 and 40±3 μg/g on fresh weight basis (FW) (Table 2). The supernatant 186±5 ml obtained following the precipitation of pigments was analyzed for mineral composition using ICP. Macro and micro minerals composition of liquid extract is presented in Table 3. The lipid yield was 0.66±0.04 (DW). Refined Carrageenan yield was 35.97±1.46% (DW) (Table 2), having 1040±36 g/cm$^2$ gel strength (1% gel; 20 degree C.). Cellulose yield was 3.24±0.17% (DW). The experiment was performed in triplicates.

Example 5

50 g of *Sarconema scinaioides* fresh sample was processed for extraction of multiple products in an integrated manner as in example 4 except the lipid extraction where the sample was processed four times with chloroform and methanol (1:2 v/v). The R-PE and R-PC contents were 242±10 and 53±9 μg/g fresh weight basis (FW). The supernatant 165±5 ml obtained following the precipitation of pigments was analyzed for mineral composition using ICP. Macro and micro minerals composition of liquid extract is presented in Table 3. The lipid yield was 1.08±0.17 (DW). Carrageenan yield was 29.81±0.2% (DW) (Table 2), having <100 g/cm$^2$ gel strength (1% gel; 20 degree C.). Cellulose yield was 2.60±0.14% (DW) (Table 2). The experiment was performed in triplicates.

Example 6

A 50 g of washed fresh *Gracilaria dura* sample was homogenized in 100 ml of 0.1M chilled phosphate buffer (pH 6.8) using mixer grinder and incubated for 12 hrs at 4° C.

Following the incubation, the contents in phosphate buffer was mixed thoroughly and centrifuged at 7000 rpm at 4° C. for 15 minutes. The supernatant containing crude pigment was collected and residual part was further subjected to pigment extraction as above using 50 ml of phosphate buffer. The supernatant fraction with pigments was subjected to ultra membrane filtration. The filtrate was dissolved in phosphate buffer and R-phycoerythrine (R-PE) and R-phycocyanine (R-PC) content were quantified using spectrophotometric method. The absorbance was read in double beam UV-Vis spectrophotometer (UV-160, Shmadzu, Japan) at 280, 564, 618 and 730 nm. The concentration of pigments R-PE and R-PC were calculated according to equation given by Sampath-Wiley et al. (2007). The R-PE and R-PC contents were 329.76 μg/g and 129.64 μg/g fresh weight basis (FW) which were comparable to those values obtained through ammonium sulfate precipitation. Ultra membrane filtration of pigment solution could be avoided the use of ammonium sulfate while in large scale production Example 7

The solvents (chloroform and methanol) used for lipid extraction were recovered using rotary evaporator. The chloroform was recovered from greenish organic layer while methanol was recovered from collected upper aqueous layer. To find out the usefulness of recovered solvents, both recycled chloroform and recycled methanol were used up to three times in experiment with 50, 40 and 35 g *Gracilaria dura*. The lipid yields were comparable for each cycle (0.94, 0.91, and 0.85% DW) indicating the possible reusability of solvents.

Example 8

The optimization of cellulose hydrolysis was carried out using commercial enzyme cellulase 22086 (Novozyme, Denmark). The cellulose hydrolysis was optimized with respect to enzyme dosage and incubation period. For this 0.5 g extracted cellulose (*G. acerosa*) was hydrolyzed with different concentration of cellulase i.e. 1%, 2% and 5% v/v in a fix volume (30 ml) of sodium acetate buffer (pH 4.8) and incubated for different time intervals ranging from 12 to 48 h at 45 degree C. on an orbital shaker. Samples were taken out periodically after an interval of 12 h each and centrifuged. The reducing sugar was measured spectrophotometrically using 3,5-dinitrosalisylic acid (DNS) method. Fermentation of the cellulose hydrolysate was carried out using yeast strain *Saccharomyces cerevisiae*, (MTCC No. 180, Institute of Microbial Technology, Chandigarh, India). The hydrolysate obtained after enzymatic hydrolysis was enriched with peptone (5 g/L) and yeast extract (3 g/L). The fresh yeast culture ($10^9$ CFU/mL) was then inoculated in the fermentation broth. Fermentation was carried out at a temperature of 28±2° C. on an orbital shaker with shaking speed of 120 rpm for an incubation period ranging from 12 to 48 h. Samples were withdrawn regularly at 12 h interval and analyzed for ethanol yield and residual reducing sugars by GC-MS and DNS method, respectively. The optimized condition for the hydrolysis was 2% cellulase enzyme, hydrolysis period 36 h and temperature 45° C. respectively. The hydrolysis of cellulose extracted from *G. acerosa* yielded 920±5 mg/g reducing sugar with conversion efficiency of 83.63%. Fermentation of hydrolysate with *S. cerevisiae* for 12 h (optimal period) produced 418±3 mg/g bioethanol corresponding to a conversion efficiency of 89.08%.

Example 9

500 g *G. acerosa* fresh sample was processed for extraction of multiple products in an integrated manner as described in example 1. All experimental components were increased proportionately w.r.t. the biomass. Pigments were extracted with 1 L and 0.5 L of phosphate buffer in two cycles. Total lipids were recovered using repeated extraction with 0.5 L of solvent Chloroform:Methanol (1:2) till greenish organic layer appeared. The residue obtained after lipid extraction was mixed with 2.5 L distilled water and autoclaved at 120 degree C. for 1.5 hours followed by centrifugation and freezing and thawing. Residual pulp (31.25 g) remaining after agar extraction was bleached with 11.25 g $NaClO_2$ in 0.47 L of sodium acetate buffer at 60 degree C. for 8 h. The bleached samples were washed with water till neutrality. Thereafter, the samples were treated with 0.19 L of 0.5 M NaOH solution at 60 degree C. for 12 h. The alkali treated mass was washed with water till neutrality. The neutralized biomass was re-suspended in 0.125 L of 5% v/v hydrochloric acid and heated up to boiling. The resultant slurry was kept overnight at room temperature, followed by washing with water to remove the excess acid and dried to obtain cellulose. The R-PE and R-PC contents were 403 and 297 µg/g (FW). 1550 ml of the supernatant obtained following the precipitation of pigments was used for analysis of minerals using ICP. Lipid yield was 1.45% (DW). Agar yields was 23.44% (DW), having 1200 g/cm² gel strength (1.5% gel; 20 degree C.), and 41 degree C. gelling temperature. Cellulose yield was 9.6% (DW).

Example 10

10 g of dry *G. dura* sample was soaked in tap water for 1 h at room temperature. Thereafter, the water was discarded, while seaweed was added to distilled water (seaweed:water=1:35, w/v) and autoclaved at 120 degree C. for 1.5 h. The cooked materials were homogenized and boiled with clarifying agents (charcoal and Celite) and filtered over a Celite bed under vacuum pressure. The filtrate was then frozen at minus 20 degree C. for 15 h and then thawed. The contents were then taken in a cloth and the water squeezed out to the maximum extent possible. The residue was then air dried at ambient temperature (30-35° C.) and subsequently oven dried at 50 degree C. for 6 h. Agar yield was 25.15±0.78% (based on dry weight) having 250±10 g/cm² gel strength (1.5% gel; 20 degree C.), and 33±0.5 degree C. gelling temperature. The experiment was performed in triplicates.

Example 11

10 g of dry *G. acerosa* sample was pre-treated with 0.5% acetic acid for 1 h and washed with tap water. The washed material was processed for agar extraction as per example 7. Agar yield was 24.50±0.70% (based on dry seaweed), having 423±15 g/cm² gel strength (1.5% gel; 20 degree C.), and 38.5±0.5 degree C. gelling temperature. The experiment was performed in triplicates.

Example 12

10 g of dry *G. pusillum* sample was treated with 0.5% acetic acid for 1 h and washed with tap water. The washed material was processed for agar extraction as per example 7. Agar yield was 25.23±0.50% (based on dry seaweed), having 750±30 g/cm² gel strength (1.5% gel; 20 degree C.), and 44±0.5 degree C. gelling temperature. The experiment was performed in triplicates.

Example 13

10 g of dry *K. alvarezii* sample was added with 200 ml of 8% KOH solution and incubated at 75° C. for 2 hrs. After incubation the material was filtered through muslin cloth and filtrate was discarded. The leftover material was added in 300 ml water and neutralized with HCl and further cooked at 80 degree C. for 45 minutes. The cooked material was homogenized well and centrifuged at 7000 rpm for 3 minutes. The supernatant was collected and precipitated with 2 volume of chilled Iso-propanol. Precipitate was dried at 65 degree C. for 4 hrs. Carrageenan yield was 37.67±1.50% (DW), having 1090±36 g/cm² gel strength (1% gel; 20 degree C.). The experiment was performed in triplicates.

Example 14

10 g of dry *S. scinaioides* sample was added to 200 ml of 8% KOH solution and incubated at 75° C. for 2 hrs. After incubation the material was filtered through muslin cloth and filtrate was discarded. The leftover material was added to 300 ml water and neutralized with HCl and further cooked at 80 degree C. for 45 minutes. The cooked material was homogenized well and centrifuged at 7000 rpm for 3 minutes. The supernatant was collected and precipitated with 2 volume of chilled Iso-propanol. Precipitate was dried at 65 degree C. for 4 hrs. Carrageenan yield was 30.04±0.41% (DW), having >100 g/cm² gel strength (1% gel; 20 degree C.). The experiment was performed in triplicates.

Example 15

The agarophytic and carrageenophytic seaweed dry samples of *G. dura*, *G. acerosa* and *G. pusillum*, *K. alvarezii* and *S. scinaioides* were processed for total lipid extraction following the methods of Bligh and Dyer [Canadian Journal of Biochemistry and Biophysiology. 1959, 37(8):911-915], and lipid content were determined by the gravimetric method. Total lipids yield for *G. dura, G. acerosa, G. pusillum, K. alvarezii* and *S. scinaioides* were 1.53±0.26%, 1.34±0.08%, 1.03±0.1%, 0.68±0.04%, and 1.13±0.08 respectively. The experiment was performed in triplicates.

Example 16

The agarophytic and carrageenophytic dry samples of *G. acerosa, G. pusillum, G. dura, K. alvarezii* and *S. scinaioides* were processed for cellulose extraction following the methods of Mihranyan et al. [International Journal of Pharmaceutics. 2004, 269: 433-442]. 10 g of dried algal powder of each alga was defatted with methanol. The defatted algal powders were bleached with 36% $NaClO2$ (w/w) in 150 ml acetate buffer at 60 degree C. for 6 hrs. The bleached algal samples were washed with water till neutrality. The washed materials were treated with 60 ml of 0.5 M NaOH solution at 60 degree C. for 12 hrs. The alkali treated algal materials were washed with water until the pH reached 7, filtered and dried at room temperature. The dried materials were re-suspended in 40 ml hydrochloric acid (5% v/v) and were heated up to boiling and resultant slurry were kept overnight at 30 degree C., followed by water washing for removing the excess acid, filtered and dried to get cellulose. Cellulose yields were calculated based on initial seaweed samples used for extraction process. Characterization of Celluloses was carried out by using the instrument Fourier transforms infrared (FT-IR) Perkin-Elmer Spectrum GX FTIR (USA). The cellulose yields for *G. dura, G. acerosa, G. pusillum, K. alvarezii* and *S. scinaioides* were 9.77±0.23%, 12.20±0.45%, 3.7±0.13%, 3.45±0.22% and 2.93±0.15% respectively. The experiment was performed in triplicates.

Example 17

Figure 6:
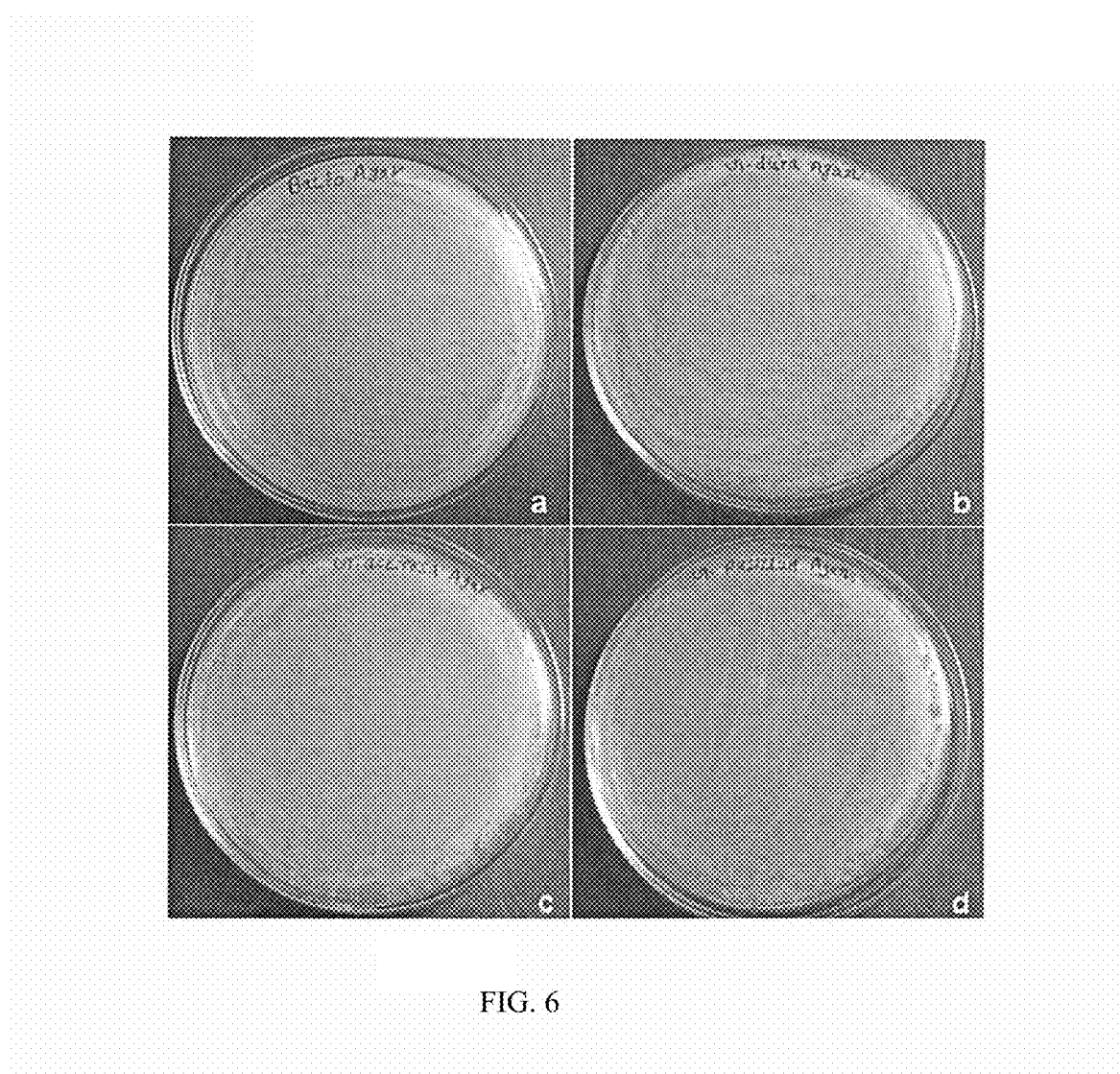
FIG. 6 depicts the comparison of growth of *E. coli* in nutrient broth supplemented with (a), 1.5% Bacto agar sourced from market, (b) 1.5% agar prepared from *Gracilaria dura*, (c) 0.75% agar from *Gelidiella acerosa* and (d) 0.75% agar from *Gelidium pusillum*.

To check the suitability of the recovered agar as solidifying medium for microbial growth, nutrient agar plates were prepared by supplementing different concentrations of extracted agar viz; 0.75% *G. acerosa* agar (Gel strength 1240 g/cm$^2$), 0.75% *G. pusillum* agar (Gel strength 1150 g/cm$^2$) and 1.5% *G. dura* agar (Gel strength 546 g/cm$^2$). The agar plates were further evaluated for microbial growth. For this, *E. coli* freshly revived from EZ competent cell (Quiazen Cat. No. 231222) was spread on agar plates and incubated at 37 degree C. for 24 hrs. The commercial sourced Bacto Agar (1.5%, Gel strength 600 g/cm$^2$) was used as a control. After 24 hrs similar growth pattern were observed on nutrient agar plates supplemented with commercial as well as extracted agar (FIG. 6). This experiment confirms that lower concentration of the extracted agar (*G. acerosa* & *G. pusillum*) could be used for microbiological application.

TABLE 1

Comparison of product yields extracted from agarophytic seaweeds by integrated process and direct extraction using conventional methods

| Products | Integrated process | Conventional methods |
|---|---|---|
| *Gelidiella acerosa* | | |
| Dry weight | 25.39 ± 0.14 | — |
| R-Phycoerythrin (µg/g FW) | 419 ± 3 | — |
| R-Phycocyanin (µg/g FW) | 303 ± 4. | — |
| Lipid (% DW) | 1.41 ± 0.10 | 1.53 ± 0.26 |
| Agar (% DW) | 23.04 ± 1.09 | 24.50 ± 0.70 |
| Cellulose (% DW) | 8.84 ± 0.5 | 9.97 ± 0.23 |
| *Gelidium pusillum* | | |
| Dry weight | 38.08 ± 0.25 | — |
| R-Phycoerythrin (µg/g FW) | 715 ± 5 | — |
| R-Phycocyanin (µg/g FW) | 99 ± 12 | — |
| Lipid (% DW) | 1.26 ± 0.05 | 1.34 ± 0.08 |
| Agar (% DW) | 24.78 ± 0.94 | 25.23 ± 0.50 |
| Cellulose (% DW) | 11.01 ± 0.7 | 12.20 ± 0.45 |
| *Gracilaria dura* | | |
| Dry weight | 12.24 ± 0.09 | — |
| R-Phycoerythrin (µg/g FW) | 340 ± 5 | — |
| R-Phycocyanin (µg/g FW) | 160 ± 5 | — |
| Lipid (% DW) | 0.94 ± 0.05 | 1.03 ± 0.11 |
| Agar (% DW) | 23.24 ± 0.55 | 25.15 ± 0.78 |
| Cellulose (% DW) | 3.57 ± 0.10 | 3.70 ± 0.13 |

TABLE 2

Comparison of product yields extracted from carrageenophytic seaweeds by integrated process and direct extraction using conventional methods

| Products | Integrated process | Conventional methods |
|---|---|---|
| *Kappaphycus alvarezii* | | |
| Dry weight | 7.52 ± 0.02 | — |
| R-Phycoerythrin (µg/g FW) | 54.0 ± 3.0 | — |
| R-Phycocyanin (µg/g FW) | 40.0 ± 3.0 | — |
| Lipid (% DW) | 0.66 ± 0.04 | 0.68 ± 0.04 |
| Carrageenan (% DW) | 35.97 ± 1.46 | 37.67 ± 1.50 |
| Cellulose (% DW) | 3.24 ± 0.17 | 3.45 ± 0.22 |
| *Sarconema scinaioides* | | |
| Dry weight | 8.08 ± 0.03 | — |
| R-Phycoerythrin (µg/g FW) | 242.0 ± 10.0 | — |
| R-Phycocyanin (µg/g FW) | 53.0 ± 9.0 | — |
| Lipid (% DW) | 1.08 ± 0.17 | 1.13 ± 0.08 |
| Carrageenan (% DW) | 29.81 ± 0.19 | 30.04 ± 0.41 |
| Cellulose (% DW) | 2.60 ± 0.14 | 2.93 ± 0.15 |

TABLE 3

Composition of liquid extract obtained from integrated process (mg/100 ml)

| Mineral | G. acerosa | G. pusillum | G. dura | K. alvarezii | S. scinaioides |
|---|---|---|---|---|---|
| Al | 0.07 ± 0.01 | 0.23 ± 0.16 | 0.08 ± 0.02 | 0.09 ± 0.01 | 0.09 ± 0.01 |
| Ca | 10.38 ± 2.25 | 14.07 ± 3.82 | 7.48 ± 3.03 | 2.50 ± 0.16 | 2.66 ± 0.37 |
| Cr | 0.05 ± 0.03 | 0.14 ± 0.10 | 0.04 ± 0.02 | 0.02 ± 0.01 | 0.02 ± 0.01 |
| Cu | 0.03 ± 0.02 | 0.07 ± 0.04 | 0.01 ± 0.01 | 0.08 ± 0.06 | 0.07 ± 0.06 |
| Fe | 0.09 ± 0.01 | 1.59 ± 1.31 | 0.11 ± 0.02 | 0.08 ± 0.01 | 0.08 ± 0.01 |
| K | 132.34 ± 2.88 | 71.31 ± 7.75 | 96.37 ± 0.62 | 144.28 ± 20.14 | 114.96 ± 2.90 |
| Mg | 12.88 ± 2.43 | 12.73 ± 1.58 | 11.61 ± 4.21 | 5.10 ± 0.40 | 5.67 ± 0.54 |
| Mn | 0.06 ± 0.05 | 0.19 ± 017 | 0.16 ± 0.05 | 0.01 ± 0.01 | 0.02 ± 0.01 |
| Na | 12.70 ± 0.49 | 18.60 ± 0.94 | 12.32 ± 0.32 | 48.59 ± 7.56 | 56.62 ± 2.04 |
| Ni | 0.01 ± 0.01 | 0.03 ± 0.02 | 0.01 ± 0.01 | 0.01 ± 0.01 | 0.01 ± 0.01 |
| Se | 0.63 ± 0.33 | 0.57 ± 0.32 | 0.42 ± 0.31 | 0.16 ± 0.04 | 0.12 ± 0.04 |
| Zn | 1.76 ± 0.32 | 1.03 ± 0.05 | 0.30 ± 0.26 | 0.12 ± 0.03 | 0.09 ± 0.01 |
| Total | 175.41 ± 7.28 | 121.28 ± 8.54 | 128.87 ± 6.64 | 203.01 ± 15.18 | 180.42 ± 0.96 |
| $(NH4)_2SO_4$ (g) | 25.68 ± 0.08 | 25.79 ± 0.08 | 25.39 ± 0.10 | 34.06 ± 0.19 | 34.04 ± 0.43 |
| $PO_4^{3-}$ (g) | 0.92 ± 0.02 | 0.90 ± 0.02 | 0.78 ± 0.02 | 0.760 ± 0.02 | 0.859 ± 0.02 |

From tables 1 and 2 it may be observed that the product yield as obtained by the claimed integrated process is lower as compared to that obtained using the conventional methods. This owes to the fact that the present process claims the recovery of multiple products from fresh seaweed biomass in an integrated manner. The products yield obtained in the integrated process is marginally less over direct extraction from primary biomass using conventional methods due to the loss of small fraction of biomass in each sequential extraction step.

- The developed process enables the recovery of a spectrum of bioproducts of commercial importance in an integrated manner along with bioethanol.
- The yields of products are comparable with those obtained individually from primary biomass following conventional methods.
- The sequential extraction of products helped in recovering a high quality phycocolloid (agar) having superior physicochemical properties than that obtained individually from primary biomass following conventional methods.
- Complete utilization of seaweed raw material without any leftover solid waste.
- Reduction by up to 85% in chemicals usage in cellulose extraction in downstream process.
- The process demonstrates the reusability of solvents (three times) in the subsequent extraction of lipids without compromising the yield.

We claim:

1. An integrated process to recover a spectrum of bioproducts from fresh seaweeds, the process comprising the steps of:
    performing an aqueous extraction on the fresh seaweeds to from a first residue and a supernatant;
    and performing a solvent extraction on the first residue to recover a lipid product and a second residue,
    wherein the step of performing an aqueous extraction comprises: homogenizing the fresh seaweeds in a phosphate buffer having a pH in the range of 6.8 to 7.0; incubating the homogenized fresh seaweeds at a temperature in the range of 4 to 6 degree C. for a time period of 10 to 12 hours; separating the first residue and the supernatant with a centrifuge, the centrifuge operating from 5000 to 7000 rpm for a period of 12 to 15 minute, the separation occurring at a temperature of 4 to 10 degree C.,
    wherein the step of performing a solvent extraction comprises: extracting the lipid product from the first residue using chloroform and methanol mixed in a ratio of 1:2 v/v; separating the lipid product from the second residue with a centrifuge operating from 4000 to 5000 rpm for a period of 10 to 15 minutes, the separation occurring at a temperature of 4 to 10° C., and wherein the supernatant comprises pigments and protein.

2. The integrated process of claim 1, further comprising:
    precipitating the pigments from the supernatant with ammonium sulphate; and
    separating the precipitated pigments with a centrifuge, the centrifuge operating from 6500 to 8000 rpm for a period of 12 to 15 minutes, the precipitated pigment separation occurring at a temperature of 4 to 10 degrees C.

3. The integrated process of claim 1, further comprising:
    filtering the supernatant with a membrane filter to concentrate the pigments.

4. The integrated process of claim 1, wherein the fresh seaweeds comprises an agarophyte.

5. The integrated process of claim 4, further comprising:
    performing a polysaccharide extraction process on the second residue to recover an agar product and a third residue.

6. The integrated process of claim 5, wherein the step of performing a polysaccharide extraction process further comprises:
    drying the second residue at a temperature in the range of 60 to 65 degree C. for 50 to 60 minutes;
    cooking the dried second residue in a cooking solution of fresh algal biomass and distilled water present in a ratio of 1:5 w/v at a temperature of 115 to 120 degree C. for 80 to 90 minutes;
    homogenizing the cooked second residue with a mixer grinder; and
    separating an agar supernatant and the third residue with a centrifuge operating at 6000 to 7000 rpm for a period of 4 to 6 minutes, the separation occurring at a temperature of 40 to 60 degrees C.

7. The integrated process of claim 6, further comprising:
    forming a gel of the agar supernatant at a temperature of 25 to 30 degrees C.;
    freezing the gel at a temperature of −15 to −20 degrees C. for 12 to 15 hours;

thawing the frozen gel to obtain the agar product; and
drying the agar product at a temperature of 60 to 65 degrees C. for 10 to 12 hours.

8. The integrated process of claim 1, wherein the fresh seaweeds comprise a carrageenophyte.

9. The integrated process of claim 8, further comprising:
performing a polysaccharide extraction process on the second residue to recover a carageenan product and a third residue.

10. The integrated process of claim 9, wherein the step of performing a polysaccharide extraction process further comprises:
drying the second residue at a temperature in the range of 60 to 65 degree C. for 50 to 60 minutes;
cooking the dried second residue in an 8% KOH solution at a temperature of 70 to 72 degrees C. for 105 to 120 minutes;
filtering the cooked second residue;
washing the filtered second residue with tap water;
cooking the washed second residue with water at a temperature of 75 to 78 degrees C. for 40 to 45 minutes;
homogenizing the cooked second residue and separating the cooked second residue into a cooked supernatant and the third reside with a centrifuge operating at 6000 to 7000 rpm for 3 to 5 minutes;
precipitating carageenan from the cooked supernatant in chilled isopropanol; and
drying the precipitated carrageenan at a temperature of 60 to 65 degrees C. for 4 to 6 hours.

11. The integrated process of claim 5 further comprising:
performing a cellulosic extraction process on the third residue to recover a cellulose product.

12. The integrated process of claim 10, wherein the step of performing a cellulosic extraction process further comprises:
drying the third residue;
soaking the third residue in an acetate buffer having a pH of 4.5 containing 36% $NaClO_2$ (w/w) for bleaching of the third residue;
washing the bleached third residue with water;
treating the washed third residue with a 0.5 M NaOH solution at a temperature of 60 to 65 degree C. for 10 to 12 hours;
washing with water to form a neutralized material;
drying the neutralized material;
treating the dried neutralized material with a 5% (v/v) solution of hydrochloric acid to form a treated material;
boiling the treated material;
incubating the boiled treated material at a temperature of 25 to 30 degrees C. for 10 to 14 hours to form a slurry;
washing the slurry with water; and
drying the slurry to form the cellulose product.

13. The integrated process of claim 9 further comprising:
performing a cellulosic extraction process on the third residue to recover a cellulose product.

14. The integrated process of claim 13, wherein the step of performing a cellulosic extraction process further comprises:
drying the third residue;
soaking the third residue in an acetate buffer having a pH of 4.5 containing 36% $NaClO_2$ (w/w) for bleaching of the third residue;
washing the bleached third residue with water;
treating the washed third residue with a 0.5 M NaOH solution at a temperature of 60 to 65 degree C. for 10 to 12 hours;
washing with water to form a neutralized material;
drying the neutralized material;
treating the dried neutralized material with a 5% (v/v) solution of hydrochloric acid to form a treated material;
boiling the treated material;
incubating the boiled treated material at a temperature of 25 to 30 degrees C. for 10 to 14 hours to form a slurry;
washing the slurry with water; and
drying the slurry to form the cellulose product.

* * * * *

UNITED STATES PATENT AND TRADEMARK OFFICE
CERTIFICATE OF CORRECTION

PATENT NO.         : 10,000,579 B2
APPLICATION NO.    : 15/109232
DATED              : June 19, 2018
INVENTOR(S)        : Reddy et al.

It is certified that error appears in the above-identified patent and that said Letters Patent is hereby corrected as shown below:

In the Claims

Column 21, Line 32, delete "10" and insert --11--

Signed and Sealed this
Second Day of October, 2018

Andrei Iancu
*Director of the United States Patent and Trademark Office*